United States Patent
Mandal et al.

(10) Patent No.: US 6,559,322 B1
(45) Date of Patent: May 6, 2003

(54) PROCESS FOR PREPARATION OF A LACTONE FROM A CYCLIC KETONE

(75) Inventors: Deendayal Mandal, Maharashtra (IN); Absar Ahmad, Maharashtra (IN); Mohammed Islam Khan, Maharashtra (IN); Rajiv Kumar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/032,203

(22) Filed: Dec. 21, 2001

(51) Int. Cl.$^7$ .................... C07D 313/16; C07D 309/00; C07D 407/00

(52) U.S. Cl. ........................ 549/263; 549/200; 549/263; 549/271; 549/272; 549/273; 549/295

(58) Field of Search ................................. 549/200, 263, 549/271, 272, 273, 295

(56) References Cited

FOREIGN PATENT DOCUMENTS

JP          62-236497          10/1987

OTHER PUBLICATIONS

Lemiere et al. (Z. Allg. Mikrobiol. (1975), 15(2), 89–92).*
Rao et al. (INdian J. of Chem. Sect. B, 23B(5), 483–5).*
M.J. Taschner et al., "The Enzymatic Baeyer–Villiger Oxidation: Enantioselective Synthesis of Lactones from Mesomeric Cyclohexanones", J. American Chemical Soc., vol. 110, 1988, pp. 6892–6893.
F. Secundo et al., "Cyclohexanone Monooxygenase Catalyzed Oxidation of Methyl Phenyl Sulfide and Cyclohexanone with Macromolecular NADP in a Membrane Reactor", Biotechnology Letters, vol. 15, No. 8, Aug. 1993, pp. 865–870.
A. Bhaumik et al., "Baeyer–Villiger rearrangement catalysed by titanium silicate molecular sieve (TS–1)/$H_2O_2$ system", Catalysis Letters, vol. 40, 1996, pp. 47–50.

* cited by examiner

Primary Examiner—Sabiha Qazi
(74) Attorney, Agent, or Firm—Darby & Darby

(57) ABSTRACT

The present invention provides a new biocatalyst whole cell system for converting cyclic ketones such as cyclopentanone/cyclohexanone to the corresponding lactones such as valerolactone/caprolactone. Another novel aspect of the present invention is that biocatalyst fungus *Fusarium oxysporum* f.sp. ciceri NCIM 1282 species has been found to be an efficient biocatalyst system for any biotransformation for the first time.

16 Claims, No Drawings

PROCESS FOR PREPARATION OF A LACTONE FROM A CYCLIC KETONE

FIELD OF THE INVENTION

The present invention relates to a process for the preparation of a lactone from the corresponding cyclic ketone. More particularly, the present invention relates to a process for biotransformation of a cyclic ketone to the corresponding lactone. The process of this invention comprises an efficient, easy and environmentally friendly method for biotransformation of cyclic ketones to corresponding lactones using naturally occurring biomaterials such as fungi.

BACKGROUND OF THE INVENTION

Lactones are an important class of molecules for the food industry because of their highly aromatic fruity aroma. Lactones, particularly caprolactone and valerolactone, are also used as monomers for preparing biodegradable polymers. Additionally, the oxidation of ketones to esters and lactones by the Baeyer—Villiger reactions is a reliable and highly useful transformation in synthetic chemistry.

The most common and conventional method for preparing lactones from cyclic ketones is based on the use of reagents like peroxycarboxylic acids (e.g. peracetic acid). The main drawback of such chemical methods using per-acids is that they are of hazardous nature and are detrimental to the environment. A catalytic method for the oxidation of ketone to lactones using solid titanium silicate (TS-1) catalyst and dilute hydrogen peroxide (H2O2) has been reported (see A. Bhaumik, P. Kumar and R. Kumar, Catalysis Letters, volume 40, year 1996 and page number 47–50). However, in the case of chemical, catalytic method involving TS-1 and dilute $H_2O_2$, the efficiency of utilization of $H_2O_2$ is low, rendering the process costly and uneconomic for commercial exploitation.

Enzymatic transformation of cyclohexanone and cyclopentanone to corresponding lactones using enzymes isolated from microorganism Acinetobacter has been reported (see M. J. Taschner and D. J. Black, Journal of American Chemical Society, Vol. 110, year 1988, p. 6892; F. Secundo, G. Carrea, S. Riva, E. Battistel, D. Bianchi, *Biotechnology Letters*, Vol. 15, 1993, p. 865) and *Nocardia globerula* C11 (see D. B. Norris and P. W. Trudgil, *Biochemical Journal*, Vol. 12, 1971, p.3737). Certain strains of Fusarium species are claimed to be active biocatalysts for styrene epoxidation (Japanese patent Jpn. Kokai Tokkyo Koho, No. JP 62236497, 1987).

The main drawback of prior art biological methods using isolated enzymes and co-factors like NADPH is that the isolation of enzyme is cumbersome and time consuming. Further, the use of very costly co-factors makes the process economically unattractive. Another disadvantage of using isolated enzymes and co-factors like NADPH is that the isolation and separation of product from the reaction mixture is tedious.

OBJECTS OF THE INVENTION

The main object of the present invention is to provide a new process for the biotransformation of cyclic ketones to lactones obviating the above mentioned drawbacks.

Another object of the present invention is to use the whole fungal mycelial mass as biocatalyst where the separation of the biocatalyst from the product mixture is carried out easily by conventional methods like filtration or centrifugation.

Yet another object of the present invention is to carry out the biotransformation without using any extremely added expensive co-factor like NADPH.

Yet another object of the present invention is to use water as a reaction medium in an environmentally friendly reaction conditions.

SUMMARY OF THE INVENTION

Accordingly, the present invention provides a process for the preparation of a lactone from the corresponding cyclic ketone, comprising treating wet fungal mycelia with an alcoholic solution of a cyclic ketone substrate at a temperature in the range of 15 to 40° C. for a period ranging between 2 to 200 hours and separating the biomass to obtain the lactone.

In one embodiment of the invention, the cyclic ketone used is selected from C5 to C6 ketones, preferably cyclopentanone and cyclohexanone.

In a further embodiment of the invention, the alcohol used to prepare the alcoholic solution of the cyclic ketone substrate is ethanol.

In another embodiment of the invention, the wet fungal mycelia is obtained by growing the fungus *Fusarium oxysporum* f. sp. ciceri (NCIM 1282) species in a culture medium for a period of at least 2 hours at a temperature ranging between 15 to 40° C. under aseptic conditions, separating the biomass, washing, and then incubating the whole reaction mixture at 15 to 40° C. under shaking conditions and atmospheric pressure.

In one embodiment of the invention, the biomass is separated by centrifugation or filtration.

In another embodiment of the invention, the biomass is washed several times with sterile water.

In a further embodiment of the invention, the whole reaction mixture is incubated while shaking at 200 rpm.

In another embodiment of the invention, the culture medium comprises malt extract-glucose-yeast extract -peptone.

In another embodiment of the invention the concentration of the substrate per gram of the wet fungal mycelia is in the range of 1 to 50 mg, preferably 3–30 mg substrate per gram of the wet fungal mycelia and most preferably in the range of 5–10 mg substrate per gram of the wet fungal mycelia.

In yet another embodiment of the invention, the reaction between substrate and wet fungal mycelia is preferably carried out in water with the ratio of wet fungal mycelia to water being in the range of 1 and 100 (w/w).

In yet another embodiment of the invention, the incubation/reaction temperature is in the range of 23–33° C., preferably 25–29° C.

DETAILED DESCRIPTION OF THE INVENTION

The invention resides in a biotransformation process for the conversion of a cyclic ketone to the corresponding lactone using wet fungal mycelia. The cyclic ketone substrate is preferably in the form of an alcoholic solution. While any lower alcohol can be used, it is preferred to use ethanol to form the solution of the cyclic ketone. The alcoholic solution of the cyclic ketone can be prepared using any techniques known in the art.

The wet fungal mycelia is treated with the alcoholic solution of a cyclic ketone substrate preferably at a temperature in the range of 15 to 40° C. for a period ranging between 2 to 200 hours. After the treatment, the biomass is separated to obtain the lactone. The lactone obtained can be purified if desired. The cyclic ketone used is selected from C5 to C6 ketones, such as cyclopentanone or cyclohexanone.

The wet fungal mycelia is obtained by growing the fungus *Fusarium oxysporum* f. sp. ciceri (NCIM 1282) species in a culture medium for a period of at least 2 hours at a temperature ranging between 15 to 40° C. under aseptic conditions, separating the biomass by centrifugation or filtration, washing several times with sterile water, and then incubating the whole reaction mixture at 15 to 40° C. under shaking conditions of about 200 rpm and atmospheric pressure. The fungus *Fusarium oxysporum* f. sp. ciceri (NCIM 1282) species can be grown in any conventional and known culture medium. The culture medium can for example comprise malt extract-glucose-yeast extract -peptone (MGYP).

*Fusarium oxysporum* f. sp. ciceri (NCIM 1282) species acts as a biocatalyst for the preparation of lactone from the corresponding cyclic ketone. To the applicants knowledge, there is no disclosure in the art teaching the use of *Fusarium oxysporum* f. sp. ciceri (NCIM 1282) species as biocatalysts.

The concentration of the substrate per gram of the wet fungal mycelia is in the range of 1 to 50 mg, preferably 3–30 mg and most preferably in the range of 5–10 mg substrate per gram of wet fungal mycelia. Above 50 mg substrate per gram of wet fungal mycelia the process becomes very slow from practical utility point of view. Reaction between substrate and wet fungal mycelia is preferably carried out in water with ratio of wet fungal mycelia to water being in the range of 1 to 100 (w/w). Temperature of incubation of the *Fusarium oxysporum* f. sp. ciceri (NCIM 1282) and subsequent reaction is ideally between 15 to 40° C. A preferred range is 23–33° C., more preferably 25–29° C.

The whole mycelialmass, instead of isolated enzyme, is used for biotransformation of ketones. The need to add externally expensive co-factor like NADPH or NADP is avoided completely in the present process. The reduction-oxidation process is extra cellular, with the reaction occurring in solution and not inside the cell of fungus. As a result it is not necessary to use cumbersome extraction processes to recover the product from fungal mycelial biomass. It is found that the *Fusarium oxysporum* f. sp. ciceri (NCIM 1282) is a highly selective biocatalyst for the biotransformation of cyclic ketones to lactones.

The following examples are given by way of illustration and should not be construed as limiting the scope of the invention.

EXAMPLE 1

10 g of the wet fungal mycelial mass (*Fusarium oxysporum* f. sp. ciceri (NCIM 1282)), grown for 96 h in a malt extract-glucose-yeast extract -peptone (MGYP) culture medium, separated from the medium by centrifugation, washed several times with sterile water through centrifugation, was taken in 100 ml sterile distilled water in 500 ml Erlenmeyer flask. A solution of 100 mg of cyclohexanone in 0.5 g ethanol was added and incubated at 27° C. Samples were collected periodically by filtration of solution containing the fungus under sterile condition. Each sample was characterized by gas chromatography (GC) and gas chromatography coupled with Mass spectrometry (GCMS). Results are given in Table-1.

TABLE 1

| Time, h | Conversion, mole % | Selectivity of products % | |
|---|---|---|---|
| | | Cyclohexanol | Caprolactone |
| 24 | 19.8 | 100 | 0.0 |
| 48 | 31.5 | 100 | 0.0 |
| 72 | 39.0 | 100 | 0.0 |
| 96 | 86.8 | 67.0 | 33.0 |
| 120 | 100 | 0.0 | 100 |

EXAMPLE 2

15 g of wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 100 mg of cyclohexanone in 0.5 g ethanol was added and incubated at 27° C. Samples were collected periodically by filtration of solution containing fungus under sterile condition. Each sample was characterized by gas chromatography. The results are given in Table 2 below.

TABLE 2

| Time, h | Conversion, mole % | Selectivity of products % | |
|---|---|---|---|
| | | Cyclohexanol | Caprolactone |
| 24 | 27.4 | 100 | 0.0 |
| 48 | 45.6 | 100 | 0.0 |
| 60 | 76.5 | 18.2 | 81.8 |
| 72 | 100 | 0.0 | 100 |

EXAMPLE 3

20 g of wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 100 mg of cyclohexanone in 0.5 g ethanol was added and incubated at 27° C. Samples were collected periodically by filtration. Each sample was characterized by gas chromatography. Results are given below in Table 3.

TABLE 3

| Time, h | Conversion, mole % | Selectivity of products % | |
|---|---|---|---|
| | | Cyclohexanol | Caprolactone |
| 24 | 35.5 | 100 | 0.0 |
| 36 | 48.6 | 100 | 0.0 |
| 48 | 69.4 | 68.6 | 31.3 |
| 60 | 100 | 0.0 | 100 |

EXAMPLE 4

30 g of wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 100 mg of cyclohexanone in 0.5 g ethanol was added and incubated at 27° C. Samples were collected periodically by filtration of solution containing the fungus under sterile condition. Each sample was characterized by GC. The results are given in Table 4 below.

TABLE 4

| | | Selectivity of products % | |
|---|---|---|---|
| Time, h | Conversion, mole % | Cyclohexanol | Caprolactone |
| 15 | 35.5 | 100 | 0.00 |
| 30 | 59.6 | 84.1 | 15.9 |
| 42 | 80.4 | 12.7 | 87.3 |
| 48 | 100 | 0.00 | 100 |

EXAMPLE 5

30 g of wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 400 mg of cyclohexanone in 0.5 g ethanol was added and incubated at 27° C. Samples were collected periodically by filtration of solution containing fungus under sterile condition and characterized by G.C. Results are given in Table 5 below:

TABLE 5

| | | Selectivity of products % | |
|---|---|---|---|
| Time, h | Conversion, mole % | Cyclohexanol | Caprolactone |
| 24 | 35.3 | 100 | 0.0 |
| 48 | 60.5 | 81.8 | 18.2 |
| 96 | 84.2 | 25.1 | 74.9 |
| 120 | 100 | 0.0 | 100 |

EXAMPLE 6

30 g of wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 600 mg of cyclohexanone in 0.5 g ethanol was added and incubated at 27° C. Samples were collected periodically by filtration of solution containing fungus under sterile condition. Each sample was characterized by gas chromatography. The results are given in Table 6 below:

TABLE 6

| | | Selectivity of products % | |
|---|---|---|---|
| Time, h | Conversion, mole % | Cyclohexanol | Caprolactone |
| 24 | 23.6 | 100 | 0.0 |
| 72 | 58.8 | 83.4 | 16.6 |
| 96 | 81.4 | 64.1 | 35.9 |
| 120 | 100 | 0.0 | 100 |

EXAMPLE 7

30 g of wet fungal mycelial mass (*Fusarium oxysporum* f. sp. ciceri (NCIM 1282)), grown for 96 h in MGYP culture medium, separated from the medium by centrifugation, washed several times with sterile water through centrifugation, was taken in 100 ml sterile distilled water in 500 ml Erlenmeyer flask. A solution of 800 mg of cyclohexanone in 0.5 ethanol was added and incubated at 27° C. Samples were collected periodically by filtration of solution containing fungus under sterile conditions. Each sample was characterized by GC. The results are given in Table 7.

TABLE 7

| | | Selectivity of products % | |
|---|---|---|---|
| Time, h | Conversion, mole % | Cyclohexanol | Caprolactone |
| 24 | 21.7 | 100 | 0.0 |
| 48 | 34.7 | 100 | 0.0 |
| 72 | 50.0 | 100 | 0.0 |
| 96 | 59.5 | 84.9 | 15.1 |
| 120 | 70.4 | 77.5 | 22.2 |
| 144 | 100 | 0.0 | 100 |

EXAMPLE 8

This experiment illustrates the effect of reaction temperature on the conversion and selectivity. 15 g of the wet fungal mycelial mass (*Fusarium oxysporum* f. sp. ciceri (NCIM 1282)), grown for 96 h in a MGYP culture medium, separated from the medium by centrifugation, washed several times with sterile water through centrifugation, was taken in 100 ml sterile distilled water in 500 ml Erlenmeyer flask. A solution of 100 mg of cyclohexanone in 0.5 g ethanol was added and incubated at different temperatures. Samples were collected at 72 hrs by filtration of solution containing fungus under sterile condition. Each sample was characterized by GC. The results are given in Table 8 below:

TABLE 8

| | | Selectivity of products % | |
|---|---|---|---|
| Time, h | Conversion, mole % | Cyclohexanol | Caprolactone |
| 18 | 20.5 | 100 | 0.0 |
| 21 | 34.6 | 100 | 0.0 |
| 24 | 70.5 | 16.2 | 83.8 |
| 27 | 100 | 0.0 | 100 |
| 30 | 75.0 | 15.0 | 85.0 |
| 33 | 45.0 | 100 | 0.0 |
| 36 | 15.2 | 100 | 0.0 |

EXAMPLE 9

20 g of cultured and washed wet fungal mycelial mass (*Fusarium oxysporum* f. sp. ciceri (NCIM 1282)), as mentioned in above examples, was taken in 100 ml sterile distilled water in 500 ml Erlenmeyer flask. A solution of 100 mg of cyclopentanone in 0.5 g ethanol was added and incubated at 27° C. Samples collected periodically, as mentioned in above examples, were characterized by GC. The results are given in Table 9 below:

TABLE 9

| | | Selectivity of products % | |
|---|---|---|---|
| Time, h | Conversion, mole % | Cyclopentanol | Valerolactone |
| 14 | 2.43 | 100 | 0.0 |
| 24 | 3.01 | 100 | 0.0 |

TABLE 9-continued

| | | Selectivity of products % | |
|---|---|---|---|
| Time, h | Conversion, mole % | Cyclopentanol | Valerolactone |
| 38 | 39 | 0.0 | 100 |
| 48 | 100 | 0.0 | 100 |

It can therefore be seen that *Fusarium oxysporum* f. sp. ciceri (NCIM 1282) constitutes a new biocatalyst with the whole cell system converting cyclic ketones (such as cyclopentanone/cyclohexanone) to the corresponding lactones (valerolactone/caprolactone). Another novel aspect of the present invention is that the present biocatalyst *Fusarium oxysporum* f. sp. Ciceri NCIM 1282 species has been found to be an efficient biocatalyst for any biotransformation for the first time.

The Main Advantages of the Present Invention are:
1. The biocatalyst can be used as whole biomass (mycelium) without isolating the enzymes. The *Fusarium oxysporum* f.sp. ciceri NCIM 1282 species has not been used for any biotransformation so far except in the present invention.
2. The present biocatalyst can be used in the absence of any externally added co-factors such as NADP/NADPH which are very costly.
3. The use of naturally occurring fungi as a biocatalyst under aqueous medium in a simple and environmentally friendly manner.
4. The reduction—oxidation process is extracellular, with the reaction occurring in solution and not inside the fungus cell of fungus. This is a very important advantage from the practical utility point of view since the need to use cumbersome extraction process for recovering the product from fungal mycelial biomass is avoided.

We claim:

1. A process for the preparation of a lactone from the corresponding cyclic ketone, comprising treating wet fungal mycelia with an alcoholic solution of a cyclic ketone substrate at a temperature in the range of 15 to 40° C. for a period ranging between 2 to 200 hours and separating the biomass to obtain the lactone.

2. A process as claimed in claim 1 wherein the cyclic ketone used is selected from C5 to C6 ketones.

3. A process as claimed in claim 2 wherein the cyclic ketone used is selected from cyclopentanone and cyclohexanone.

4. A process as claimed in claim 1 wherein the alcohol used to prepare the alcoholic solution of the cyclic ketone substrate is ethanol.

5. A process as claimed in claim 1 wherein the wet fungal mycelia is obtained by growing the fungus *Fusarium oxysporum* f. sp. ciceri (NCIM 1282) species in a culture medium for a period of at least 2 hours at a temperature ranging between 15 to 40° C. under aseptic conditions, separating the biomass, washing, and then incubating the whole reaction mixture at 15 to 40° C. under shaking conditions and atmospheric pressure.

6. A process as claimed in claim 5 wherein the biomass is separated by centrifugation or filtration.

7. A process as claimed in claim 5 wherein the biomass is washed several times with sterile water.

8. A process as claimed in claim 5 wherein the whole reaction mixture is incubated while shaking at 200 rpm.

9. A process as claimed in claim 5 wherein the culture medium comprises malt extract-glucose-yeast extract-peptone.

10. A process as claimed in claim 1 wherein the concentration of the substrate per gram of the wet fungal mycelia is in the range of 1 to 50 mg.

11. A process as claimed in claim 1 wherein the concentration of the substrate per gram of the wet fungal mycelia is in the range of 3–30 mg.

12. A process as claimed in claim 1 wherein the concentration of the substrate per gram of the wet fungal mycelia is in the range of 5–10 mg.

13. A process as claimed in claim 1 wherein the reaction between substrate and wet fungal mycelia is carried out in water.

14. A process as claimed in claim 13 wherein the ratio of wet fungal mycelia to water being in the range of 1 and 100 (w/w).

15. A process as claimed in claim 1 wherein the incubation/reaction temperature is in the range of 23–33° C.

16. A process as claimed in claim 15 wherein the incubation/reaction temperature is in the range of 25–29° C.

* * * * *